(12) United States Patent
Drapeau et al.

(10) Patent No.: US 8,734,387 B2
(45) Date of Patent: May 27, 2014

(54) EXPANSION DEVICE FOR TREATMENT OF BLACK TRIANGLE DISEASE AND METHOD

(75) Inventors: Susan J. Drapeau, Cordova, TN (US); Daniel A. Shimko, Germantown, TN (US); Kip Roberts, Memphis, TN (US); Kelly B. Emerton, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/349,747

(22) Filed: Jan. 13, 2012

(65) Prior Publication Data

US 2013/0183634 A1    Jul. 18, 2013

(51) Int. Cl.
*A61M 29/00* (2006.01)
*A61C 19/06* (2006.01)

(52) U.S. Cl.
USPC ............... 604/96.01; 604/891.1; 604/95.03; 606/192; 433/82

(58) Field of Classification Search
USPC ............ 604/95.03, 95.04, 96.01, 97.01, 907, 604/912–913, 915–916, 891.1; 606/192, 606/195, 198; 433/82, 148, 215
See application file for complete search history.

(56) References Cited

U.S. PATENT DOCUMENTS

| | | | |
|---|---|---|---|
| 5,090,957 A | 2/1992 | Moutafis et al. | |
| 5,425,760 A | 6/1995 | Rosenberg | |
| 5,573,400 A | 11/1996 | Asher | |
| 6,007,334 A * | 12/1999 | Suhonen | 433/39 |
| 6,299,448 B1 * | 10/2001 | Zdrahala et al. | 433/173 |
| 6,976,842 B1 | 12/2005 | Miggantz | |
| 7,749,267 B2 | 7/2010 | Karmon | |
| 2004/0010263 A1 | 1/2004 | Boucher et al. | |
| 2009/0181345 A1 * | 7/2009 | Kfir | 433/172 |
| 2010/0015567 A1 * | 1/2010 | Elbaz et al. | 433/89 |
| 2010/0094329 A1 * | 4/2010 | Cardoso et al. | 606/192 |
| 2010/0203473 A1 * | 8/2010 | Chen | 433/141 |
| 2010/0221681 A1 * | 9/2010 | Hochman | 433/173 |
| 2010/0255444 A1 * | 10/2010 | Karmon | 433/172 |
| 2010/0266979 A1 * | 10/2010 | Karmon | 433/80 |
| 2012/0277861 A1 * | 11/2012 | Steele et al. | 623/17.12 |

FOREIGN PATENT DOCUMENTS

WO     2011051731 A2    5/2011

* cited by examiner

*Primary Examiner* — Quynh-nhu H Vu
(74) *Attorney, Agent, or Firm* — Sorell Lenna & Schmidt LLP (57) ABSTRACT

An expansion device includes an inflatable balloon moveable from an unexpanded configuration to an expanded configuration configured to pass through soft tissue between two adjacent teeth of a patient when in the unexpanded configuration. The an expansion device also includes an inflation tube having one end connected to the inflatable balloon and another end serving as an entry port for an inflation fluid. The inflatable balloon has a triangular shape when in the expanded configuration.

16 Claims, 2 Drawing Sheets

EXPANSION DEVICE FOR TREATMENT OF BLACK TRIANGLE DISEASE AND METHOD

TECHNICAL FIELD

The present disclosure generally relates to medical devices for the treatment of periodontal disease, and more particularly to an expansion device for treatment of black triangle disease and a method of use therefor.

BACKGROUND

Gingival embrasures, or black triangles, are triangular shaped spaces located between the proximal surfaces of adjacent teeth. During the early stages of periodontal disease, known commonly as gingivitis, bacteria on the teeth and near the gingiva infect and irritate the sulcus where the gingiva approximates the tooth. Gingivitis may cause the interdental gingiva, or gingival papilla, which occupy a gingival embrasure to recede, thus expanding the size of gingival embrasure or black triangle. As the interdental gingiva recedes, the teeth become loose which can force the epithelium to separate from the root of the tooth. Also, as a result of bacterial presence, inflammatory cells increasingly populate the gingival tissues. Thus, the tissue is weaker due to the disease, and attachment is lessened. Of course, further infection moves the tissue attachment further toward the apex of the tooth, causing the interdental gingiva to further recede. As disease expands the size of the gingival embrasure, the periodontal ligament which attaches the tooth to the supporting bone, and the supporting alveolar bone itself, are destroyed. The gingival embrasure is filled with plaque and bacteria. Ultimately, the tooth could be surrounded by loose, diseased, and detached gingiva. Eventually such deterioration can result in the loss of the tooth.

One conventional treatment of periodontal defects involves surgically gaining access to the tooth root surface in an effort to remove bacteria and possible infected soft tissue and to alter the periodontal pocket or obtain reattachment of the connective tissue toward the crown of the tooth. Some of the former methods accomplish this attachment by cutting away gingival tissue near the crown of the tooth and, if necessary, shaping underlying bone to create a sulcus similar in depth to a normal sulcus so that regular oral hygiene may be used to maintain attachment of the gingiva to the tooth. Of course, such treatment does not recreate the attachment of the gingiva near the crown like that which existed before any diseased condition. Such treatment also does not replace any periodontium lost to disease.

Another conventional treatment for periodontal disease involves gingival flap surgical procedures, where one or more flaps of gingival tissue are retracted from the tooth. After the tooth root is thoroughly cleaned, and diseased soft tissue is removed, these flaps are reopposed to the tooth. This disclosure describes an improvement over these prior art technologies.

SUMMARY OF THE INVENTION

Accordingly, an expansion device is provided for treatment of black triangle disease and a method of use therefor. It is contemplated that the expansion device and method of the present disclosure may be used to treat and/or prevent the progression of periodontal disease.

In one particular embodiment, in accordance with the principles of the present disclosure, the expansion device includes an inflatable balloon moveable from an unexpanded configuration to an expanded configuration configured to pass through soft tissue between two adjacent teeth of a patient when in the unexpanded configuration. The expansion device also includes an inflation tube configured to retain at least a portion of the inflatable balloon therein having an entry port for an inflation fluid. In one embodiment, the inflatable balloon has a triangular shape when in the expanded configuration.

In one embodiment, a method for treatment of periodontal disease is provided in accordance with the principles of the present disclosure. The method includes providing an expansion device having an inflatable balloon moveable from an unexpanded configuration to an expanded configuration configured to pass through soft tissue between two adjacent teeth of a patient when in the unexpanded configuration and an inflation tube configured to retain at least a portion of the inflatable balloon therein having an entry port for an inflation fluid. The expansion device is inserted into the soft tissue between the two adjacent teeth of the patient while the inflatable balloon is in the unexpanded configuration. The inflatable balloon is at least partially inflated to move the inflatable balloon from the unexpanded configuration to the expanded configuration.

In one embodiment, the expansion device includes an inflatable balloon moveable from an unexpanded configuration to an expanded configuration configured to pass through soft tissue between two adjacent teeth of a patient when in the unexpanded configuration. The expansion device further includes an inflation tube configured to retain at least a portion of the inflatable balloon therein having an entry port for an inflation fluid. The inflatable balloon has a triangular shape when in the expanded configuration. The inflatable balloon distends the soft tissue between the two adjacent teeth of the patient to fill a missing gingival tissue area when in the expanded configuration. The inflatable balloon is degradable and/or biologically resorbable. The inflation fluid includes an agent to facilitate regeneration of gingival tissue delivered in a solution or a carrier material. The inflation fluid further includes at least one anti-bacterial agent and/or at least one anti-microbial agent.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION OF THE INVENTION

The exemplary embodiments of the expansion device and related methods of use disclosed are discussed in terms of medical devices for the treatment of black triangle disease. It is envisioned that the expansion device may be employed to reattach and/or regenerate soft tissue affected by periodontal disease, such as, for example, black triangle disease. It is further envisioned that the present disclosure may be employed with other periodontal related applications, including those associated with diagnostics and therapeutics. It is contemplated that the present disclosure may be used on animals, bone models and other non-living substrates, such as, for example, in training, testing and demonstration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". The term "fluid" as used herein includes both gaseous and liquid mediums.

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of an expansion device and related methods of employing the expansion device in accordance with the principles of the present disclosure. Alternate embodiments are also disclosed. Reference will now be made in detail to the exemplary embodiments of the present disclosure, which are illustrated in the accompanying figures. Turning now to FIGS. 1-4, there is illustrated components of an expansion device in accordance with the principles of the present disclosure.

The components of the expansion device can be fabricated from biologically acceptable materials suitable for medical applications, including metals, synthetic polymers, ceramics and bone material and/or their composites, depending on the particular application and/or preference of a medical practitioner. For example, the components of the expansion device, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the expansion device may have material composites, including the above materials, to achieve various desired characteristics such as strength, rigidity, elasticity, compliance, biomechanical performance, durability and radiolucency or imaging preference. The components of the expansion device, individually or collectively, may also be fabricated from a heterogeneous material such as a combination of two or more of the above-described materials.

Figure 1:
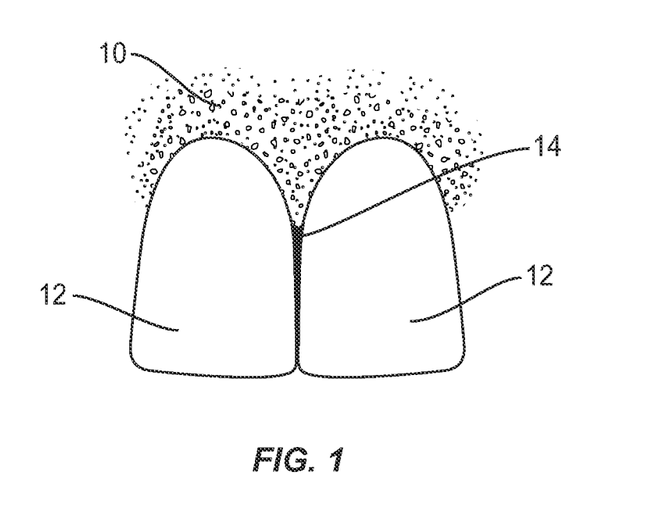
FIG. 1 is a perspective view of two adjacent teeth of a patient surrounded by healthy soft tissue.
Figure 2:
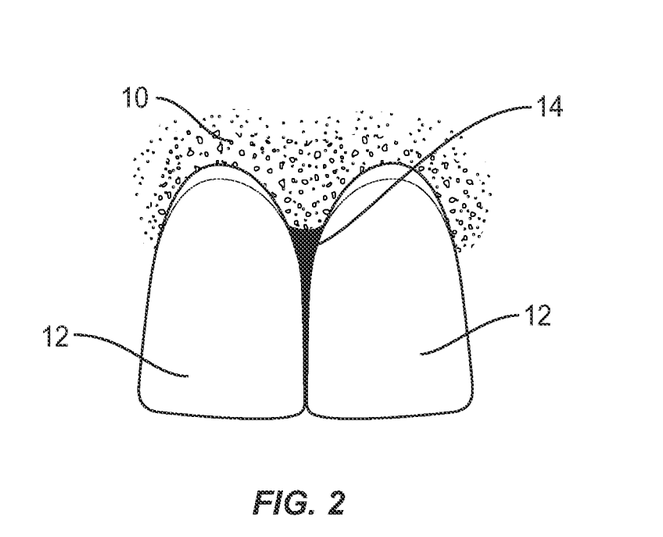
FIG. 2 is a perspective view of two adjacent teeth of a patient surrounded by soft tissue effected by periodontal disease.

When soft tissue 10 surrounding adjacent teeth 12 is healthy, interdental gingiva, or gingival papilla, fill in interdental space 14 such that interdental space 14 is minimal, as shown in FIG. 1. When soft tissue 10 is infected with disease, such as, for example, periodontal disease, the interdental gingiva which occupy interdental space 14 recede, thus expanding the size of interdental space 14, as shown in FIG. 2. Expanding the size of interdental space 14 not only interferes with the esthetics of a patient's smile, but also affects periodontal health due to retention of food debris which may cause subsequent gingival inflammation. Expansion device 30 is configured to be inserted into and expand soft tissue 10 to substantially fill interdental space 14 by restoring the interdental gingiva to avoid problems associated with an expanded interdental space.

Expansion device 30 includes an inflatable balloon 32 moveable from an unexpanded configuration to an expanded configuration. Inflatable balloon 32 is configured to pass through soft tissue 10 between adjacent teeth 12 of a patient when in the unexpanded configuration. Inflatable balloon 32 may expand or otherwise increase its volume, thus enabling inflatable balloon 32 to be deployed in a collapsed, low profile condition subcutaneously through a cannula, such as, for example, inflation tube 34, into soft tissue 10, as will be discussed. This property also enables the expansion of inflatable balloon 32 within soft tissue 10 to press against and expand soft tissue 10 surrounding adjacent teeth 12 to substantially fill interdental space 14 by restoring the interdental gingiva between teeth 12 to a healthy state.

The desired expansion of inflatable balloon 32 can be characterized by ultimate elongation properties, which indicate the degree of expansion that the material from which inflatable balloon 32 is made can accommodate prior to failure. Sufficient ultimate elongation permits inflatable balloon 32 to press against and expand soft tissue 10 surrounding adjacent teeth 12 to substantially fill interdental space 14, prior to wall failure. In one embodiment, inflatable balloon 32 will comprise material able to undergo an ultimate elongation of at least 50%, prior to wall failure, when expanded within soft tissue 10. In one embodiment, inflatable balloon 32 will comprise material able to undergo an ultimate elongation of at least 150%, prior to wall failure, when expanded within soft tissue 10. In one embodiment, inflatable balloon 32 will comprise material able to undergo an ultimate elongation of at least 300%, prior to wall failure, when expanded within soft tissue 10.

Inflatable balloon 32 is configured to predictably deform during expansion, so that inflatable balloon 32 consistently achieves a desired shape inside soft tissue 10. The shape of inflatable balloon 32, when in the expanded configuration within soft tissue 10, is desirably selected by the medical practitioner, taking into account the morphology and geometry of soft tissue 10, teeth 12 and interdental space 14. It is understood that the shape of inflatable balloon 32, when in the expanded configuration within soft tissue 10, should permit inflatable balloon 32 to press against and expand soft tissue 10 surrounding adjacent teeth 12 to substantially fill interdental space 14. In one embodiment, shown in FIG. 4, inflatable balloon 32 has a triangular or pyramidal shape when in the expanded configuration. However, it is envisioned that inflatable balloon 32 may have a shape which is conical, round, oval, or polygonal, such as, for example, square, pentagonal, hexagonal, when inflatable balloon 32 is in the expanded configuration.

In one embodiment, the shape of inflatable balloon 32 when in the expanded configuration within soft tissue 10 substantially conforms to the shape of inflatable balloon 32 outside soft tissue 10, when in an open air environment. This allows the medical practitioner to select in an open air environment a structure having an expanded shape desired to meet the targeted therapeutic result, with the confidence that the expanded shape inside soft tissue 10 will be similar in important respects.

Inflatable balloon 32 may be permeable, semipermeable, or impermeable. Providing an inflatable balloon 32 which has at least some degree of permeability will allow an inflation fluid used to fill inflatable balloon 32 to exit the interior of inflatable balloon 32 and seep into soft tissue 10 into which inflatable balloon 32 is inserted. The degree of permeability is dependent upon, for example, the type of inflation fluid and the desired rate at which the inflation fluid exits the interior of inflatable balloon 32.

In one embodiment, inflatable balloon 32 is degradable, such that inflatable balloon 32 breaks down over time within soft tissue 10. Inflatable balloon 32 may also be nonabsorbable so as to be permanent. Alternatively, inflatable balloon 32 may be resorbable so as to reabsorb into the body over time. For example, inflatable balloon be fabricated from a biocompatible, resorbable polymer including, for example, aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) or blends thereof. Polyesters include, but are not limited to, homopolymers and copolymers of lactide (which includes lactic acid, D-,L- and meso lactide), glycolide (including glycolic acid), caprolactone, p-dioxanone (1,4-dioxan-2-one), trimethylene carbonate (1,3-dioxan-2-one), alkyl derivatives of trimethylene carbonate, delta-valerolactone, beta-butyrolactone, gamma-butyrolactone, epsilon-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, alpha-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one or polymer blends thereof.

Figure 3:
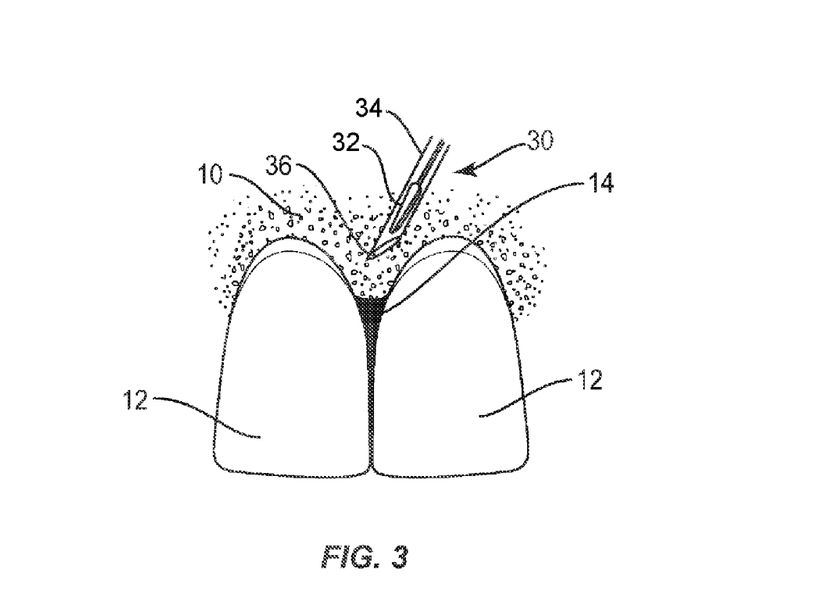
FIG. 3 is a perspective view of the two adjacent teeth of a patient surrounded by soft tissue effected by periodontal disease shown in FIG. 2 with an expansion device in accordance with the principles of the present disclosure inserted into the soft tissue with an inflatable balloon in an unexpanded configuration.
Figure 4:
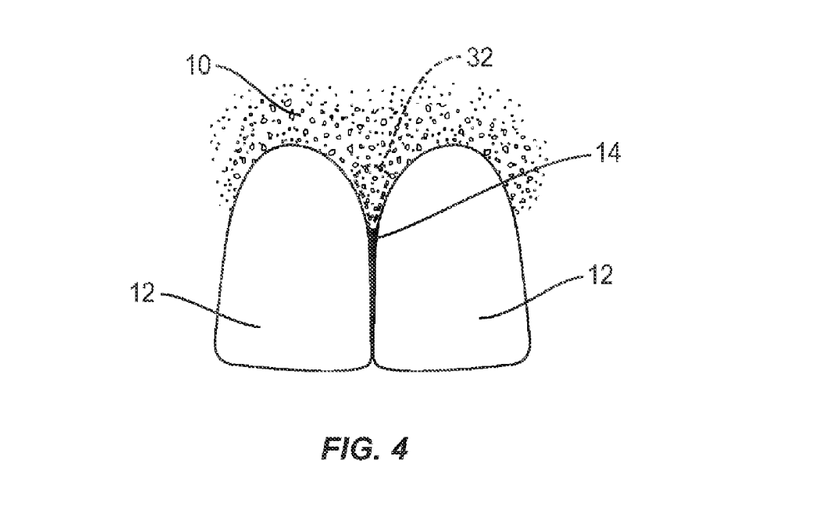
FIG. 4 is a perspective view of the two adjacent teeth of a patient surrounded by soft tissue affected by periodontal disease shown in FIG. 2 with the inflatable balloon of the expansion device shown in FIG. 3 inserted into the soft tissue in an expanded configuration.

Inflation tube 34 is a conduit, such as, for example, a cannula configured to retain at least a portion of inflatable balloon 32 therein when inflatable balloon 32 is in the unexpanded configuration, as shown in FIG. 3. Inflation tube 34 includes a distal end 36 and a proximal end, such as, for example an inflation port 38 (not shown). Distal end 36 of inflation tube 34 is configured for insertion into soft tissue 10. In one embodiment, distal end 36 is beveled to facilitate insertion of inflation tube 34 into soft tissue 10. However, it is envisioned that distal end 36 may include alternative shapes such as, for example, a tubular, triangular, pyramidal or conical shape. Inflation tube 34 has a cavity, defining a hollow interior portion, extending between distal and proximal ends 36, 38 and has openings at a distal face and a proximal face of distal and proximal ends 36, 38 so as to define a passageway through inflation tube 34 for inflatable balloon 32 and/or an inflation device. That is, inflatable balloon 32 is retained within the hollow interior portion of inflation tube 34 as inflation tube 34 is inserted into soft tissue 10. Accordingly, the diameter of inflatable balloon 32 when in the unexpanded configuration is less than the diameter of the hollow interior portion of inflation tube 34. In one embodiment, the diameter of inflatable balloon 32 when in the expanded configuration is greater than the diameter of the hollow interior portion of inflation tube 34, such that moving inflatable balloon 32 from the unexpanded configuration to the expanded configuration causes inflatable balloon 32 to exit the hollow interior portion of inflation tube 34 through distal end 36.

Inflation tube 34 has a size and shape such that distal end 36 may be inserted into soft tissue 10 adjacent interdental space 14, while retaining inflatable balloon 32 in the unexpanded configuration within the hollow interior portion of inflation tube 34. In one embodiment, the interior and exterior surfaces of inflation tube 34 each have a round cross-section. However, it is envisioned that the interior and exterior surfaces of inflation tube 34 may have alternate cross-section configurations, such as, for example, oval, oblong, triangular, rectangular, square, polygonal, irregular, uniform, non-uniform, variable and/or tapered. In one embodiment, inflation tube 34 is rigid between distal end 36 and proximal end 38. In one embodiment, at least a portion of inflation tube 34 is flexible between distal end 36 and proximal end 38 so as to allow a dentist to bend inflation tube 34 to position inflation tube 34 at the desired location relative to soft tissue 10. It is envisioned that inflation tube 34 may be comprised of a clear material such that inflatable balloon 32 is visible within inflation tube 34.

Proximal end 38 of inflation tube 34 is configured for delivery of an inflation fluid through inflation tube 34 and into inflatable balloon 32. That is, inflation fluid is inserted through inflation tube 34 and into inflatable balloon 32 to move inflatable balloon 32 from the unexpanded configuration to the expanded configuration. In one embodiment, an inflation device, such as, for example, a syringe, may be operably connected at proximal end 38 of inflation tube 34. It is envisioned that the inflation device may be connected to inflation tube 34 via a luer taper or luer-lock type connector. At least a portion of the syringe may be inserted through the interior of inflation tube 34 and into at least a portion of inflatable balloon 32. Inflation fluid, including for example, a gas or liquid, may then be injected from the syringe into inflatable balloon 32 to move inflatable balloon 32 from the unexpanded configuration to the expanded configuration. As discussed above, moving inflatable balloon 32 from the unexpanded configuration to the expanded configuration causes inflatable balloon 32 to exit distal end 36 of inflation tube 34. In one embodiment, inflatable balloon 32 is self-sealing such that inflatable balloon 32 will seal itself after the inflation device injects inflation fluid into inflatable balloon 32 and is retracted therefrom to maintain inflatable balloon 32 in the expanded configuration.

It is envisioned that inflatable balloon 32 may be inflated before or after inflatable balloon 32 is deployed from inflation tube 34 and into soft tissue 10. In one embodiment, inflatable balloon 32 is at least partially inflated with inflation fluid while inflatable balloon 32 is positioned within the hollow interior portion of inflation tube 34 in the unexpanded configuration, and inflation tube 34 is inserted into soft tissue 10. Partially inflating inflatable balloon 32 causes inflatable balloon 32 to deploy from inflation tube 34 into soft tissue 10. Inflatable balloon 32 may be further inflated after inflatable balloon 32 is inserted into soft tissue 10 by inserting additional inflation fluid into inflatable balloon 32 until inflatable balloon 32 presses against and expands soft tissue 10 surrounding adjacent teeth 12 to substantially fill interdental space 14. In one embodiment, inflatable balloon 32 is deployed from inflation tube 34 in the unexpanded configuration after inflation tube 34 is inserted into soft tissue 10. That is, inflation tube 34 is inserted into soft tissue 10. Next, inflatable balloon 32 is deployed from inflation tube 34 into soft tissue 10 while in the unexpanded configuration. Inflatable balloon 32 may then be moved from the unexpanded configuration to the expanded configuration by inserting inflation fluid into inflatable balloon 32, causing inflatable balloon 32 to press against and expand soft tissue 10 surrounding adjacent teeth 12 to substantially fill interdental space 14.

In one embodiment, the inflation fluid is a flowable material such as, for example, water, saline, or ambient air. The inflation fluid may optionally contain an anesthetic. Other suitable inflation fluids include silicone or hydrogels. It is envisioned that the inflation fluid may be curable such that the inflation fluid may harden after the inflation fluid is inserted into inflatable balloon 32 to move inflatable balloon 32 from the unexpanded configuration to the expanded configuration such that the hardened inflation fluid maintains the shape of inflatable balloon 32 in the expanded configuration, even after inflatable balloon 32 degrades or is otherwise removed.

In one embodiment, the inflation fluid includes an agent to facilitate regeneration of gingival tissue, such as, for example, soft tissue 10, selected from the group consisting of rhGDF-5, PDGF, TBF-b1, TGF-b3, FGF-18, BMP-2, BMP-7, CD-RAP, BMP-12, BMP-13 platelet rich plasma (PRP), FGF-2 and combinations thereof. The agent to facilitate regeneration of gingival tissue may be delivered in a solution or a carrier material including, but not limited to saline, alginate gel, CMC, collagen slurry, and gelatin. Other suitable carriers include biocompatible, bioresorbable and/or biodegradable biopolymers as disclosed in U.S. Pat. No. 7,993,666 "Methods and Compositions for Treating Pain Comprising a Statin", incorporated herein by reference in its entirety.

In one embodiment, the inflation fluid may include at least one bioactive substance. Bioactive substances include physiologically or pharmacologically active substances that act locally or systemically in the host. In certain applications, the inflation fluid can be used as a time-release drug delivery device for drugs or other bioactive substances that are to be delivered to the surgical site. Bioactive substances which can be readily combined with the inflation fluid include, for example, collagen, insoluble collagen derivatives, etc., and soluble solids and/or liquids dissolved therein; antiviricides, particularly those effective against HIV and hepatitis; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin or gentamicin, etc.; biocidal/biostatic sugars such as dextran, glucose, etc.; amino acids; peptides; vitamins; inorganic elements; co-factors for protein synthesis; hormones; endocrine tissue or tissue fragments; synthesizers; enzymes such as collagenase, peptidases, oxidases, etc.; polymer cell scaffolds with parenchymal cells; angiogenic agents or polymeric carriers containing such agents; collagen lattices; antigenic agents; cytoskeletal agents; cartilage fragments; living cells such as chondrocytes, bone marrow cells, mesenchymal stem cells, natural extracts, genetically engineered living cells or otherwise modified living cells; DNA delivered by plasmid or viral vectors; tissue transplants; demineralized bone powder; autogenous tissues such as blood, serum, soft tissue, bone marrow, etc.; bioadhesives, bone morphogenic proteins (BMPs); osteoinductive factor; fibronectin (FN), osteonectin (ON); endothelial cell growth factor (ECGF); cementum attachment extracts (CAE); ketanserin; human growth hormone (HGH); animal growth hormones; epidermal growth factor (EGF); interleukin-1 (IL-1); human alpha thrombin; transforming growth factor (TGF-beta); insulin-like growth factor (IGF-1); fibroblast growth factors (FGF, bFGF, etc.); periodontal ligament chemotactic factor (PDLGF); somatotropin; bone digestors; antitumor agents; immuno-suppressants; permeation enhancers, e.g., fatty acid esters such as laureate, myristate and stearate monoesters of polyethylene glycol, enamine derivatives, alpha-keto aldehydes, etc.; nucleic acids, or a combination thereof. When employed, the total amount of bioactive substance can represent from about 0.1 to about 60 weight percent of the inflation fluid.

In one embodiment, the bioactive substance comprises the family of proteins known as the transforming growth factor-beta (TGFβ) superfamily of proteins, which includes the activins, inhibins, or bone morphogenetic proteins (BMPs). In some embodiments, the bioactive substance includes at least one protein from the subclass of proteins known generally as BMPs. BMPs have been shown to possess a wide range of growth and differentiation activities. See, for example, descriptions of BMPs in the following publications: BMP-2, BMP-3, BMP-4, BMP-5, BMP-6, and BMP-7 (disclosed, for example, in U.S. Pat. No. 5,013,649 (BMP-2 and BMP-4); U.S. Pat. No. 5,116,738 (BMP-3); U.S. Pat. No. 5,106,748 (BMP-5); U.S. Pat. No. 5,187,076 (BMP-6); and U.S. Pat. No. 5,141,905 (BMP-7)); BMP-8 (disclosed in PCT WO 91/18098); BMP-9 (disclosed in PCT WO 93/00432); BMP-10 (disclosed in PCT WO 94/26893); BMP-11 (disclosed in PCT WO 94/26892); BMP-12 or BMP-13 (disclosed in PCTWO 95/16035); BMP-15 (disclosed in U.S. Pat. No. 5,635,372); BMP-16 (disclosed in U.S. Pat. No. 6,331,612); MP52/GDF-5 (disclosed in PCT WO 93/16099); or BMP-17 or BMP-18 (disclosed in U.S. Pat. No. 6,027,917). The entire disclosure of these references is herein incorporated by reference.

In one embodiment, the inflation fluid may be mixed with additional therapeutic agents. Exemplary therapeutic agents include but are not limited to IL-1 inhibitors, such Kineret® (anakinra), which is a recombinant, non-glycosylated form of the human interleukin-1 receptor antagonist (IL-1 Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dithiocarbamate, and other compounds, such as, for example, sulfasalazine.

Examples of therapeutic agents suitable for use also include, but are not limited to, an anti-inflammatory agent, or analgesic agent. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin, and tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable analgesic agents include, but are not limited to, acetaminophen, bupivicaine, fluocinolone, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

In one embodiment, the inflation fluid includes at least one anti-microbial agent. Antimicrobial agents to treat infection include by way of example and not limitation, antiseptic agents, antibacterial agents; quinolones and in particular fluoroquinolones (e.g., norfloxacin, ciprofloxacin, lomefloxacin, ofloxacin, etc.), aminoglycosides (e.g., gentamicin, tobramycin, etc.), glycopeptides (e.g., vancomycin, etc.), lincosamides (e.g., clindamycin), cephalosporins (e.g., first, second, third generation) and related beta-lactams, macrolides (e.g., azithromycin, erythromycin, etc.), nitroimidazoles (e.g., metronidazole), penicillins, polymyxins, tetracyclines, or combinations thereof.

Some exemplary antimicrobial agents include, by way of illustration and not limitation, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; cefsoranide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; chlorhexidine, cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

In one embodiment, the inflation fluid may include a statin. Statins include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+) R and (−) S enantiomers of the statin. In various embodiments, the statin may comprise a 1:1 racemic mixture of the statin.

In use, expansion device 30 is inserted into soft tissue 10 surrounding adjacent teeth 12 of the patient. In particular, distal end 36 of inflation tube 34 is inserted into soft tissue 10 while inflatable balloon 32 is retained in the hollow interior portion of inflation tube 34 in the unexpanded configuration. It is envisioned that an incision may be made in soft tissue 10 into which distal end 36 of inflation tube 34 is inserted. Alternatively, distal end 36 of inflation tube 34 may be inserted directly into soft tissue 10.

Inflatable balloon 32 is then deployed from inflation tube 34 into soft tissue 10. Inflatable balloon 32 may be at least partially inflated while inflatable balloon 32 is retained within the hollow interior of inflation tube 34 by injecting inflation fluid into inflatable balloon 32. At least partially inflating inflatable balloon 32 while inflatable balloon 32 is retained in the hollow interior portion of inflation tube 34 causes inflatable balloon 32 to deploy from inflation tube 34. That is, inflatable balloon 32 may at least partially inflated with inflation fluid while at least a portion of inflatable balloon 32 is positioned within the hollow interior inflation tube 34 in the unexpanded configuration, and inflation tube 34 is inserted into soft tissue 10, causing inflatable balloon 32 to deploy from distal end 36 of inflation tube 34 into soft tissue 10. Inflatable balloon 32 may be further inflated after inflatable balloon 32 is deployed from inflation tube 34 and into soft tissue 10 by inserting additional inflation fluid into inflatable balloon 32 until inflatable balloon 32 presses against and expands soft tissue 10 surrounding adjacent teeth 12 to substantially fill interdental space 14.

Inflatable balloon 32 may also be inflated after inflatable balloon 32 is deployed from inflation tube 34. That is, inflatable balloon 32 may be deployed from inflation tube 34 and into soft tissue 10 in the unexpanded configuration after inflation tube 34 is inserted into soft tissue 10. Inflatable balloon 32 may then be moved from the unexpanded configuration to the expanded configuration by inserting inflation fluid into inflatable balloon 32, causing inflatable balloon to press against and expand soft tissue 10 surrounding adjacent teeth 12 to substantially fill interdental space 14.

In one embodiment, inflatable balloon 32 is removed from soft tissue 10 after moving inflatable balloon 32 from the unexpanded configuration to the expanded configuration within soft tissue 10. That is, inflatable balloon 32 may be deflated by removing the inflation fluid from the interior of inflatable balloon 32 such that inflatable balloon 32 moves from the expanded configuration to the unexpanded configuration. Inflatable balloon 32 may then be removed from soft tissue 10 in the unexpanded configuration.

In one embodiment, where inflatable balloon 32 is comprised of a degradable material, inflatable balloon 32 may be left within soft tissue 10 in the expanded configuration until at least a portion of inflatable balloon 32 degrades. As inflatable balloon 32 degrades, the inflation fluid, including any agent mixed with the inflation fluid, will seep into soft tissue 10.

In one embodiment, where inflatable balloon 32 is comprised of a biologically resorbable material, inflatable balloon 32 may be left in soft tissue 10 after at least partially inflating inflatable balloon 32 until at least a portion of inflatable balloon 32 is broken down and assimilated into soft tissue 10.

In one embodiment, inflatable balloon 32 is inflated within soft tissue 10 by injecting a fluid or gas into the interior portion of inflatable balloon 32 causing inflatable balloon 32 to move from the unexpanded configuration to the expanded configuration within soft tissue 10 such that inflatable balloon 32 presses against and expands soft tissue 10 surrounding adjacent teeth 12 to substantially fill interdental space 14. Inflatable balloon 32 may then be moved from the expanded configuration to the unexpanded configuration and removed from soft tissue 10 when in the unexpanded configuration. After inflatable balloon 32 is removed from soft tissue 10 in the unexpanded configuration, inflatable balloon 32 may be filled with the inflation fluid discussed above such that inflatable balloon 32 moves from the unexpanded configuration to the expanded configuration. Inflatable balloon 32 may then be reinserted into soft tissue 10 in the expanded configuration. Insertion of the inflated balloon into soft tissue 10 can be achieved using a small incision if needed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An expansion device for treatment of periodontal disease comprising:
    an inflatable balloon moveable from an unexpanded configuration to an expanded configuration configured to pass through soft tissue between two adjacent teeth of a patient when in the unexpanded configuration; and
    an inflation tube configured to retain at least a portion of the inflatable balloon therein having an entry port for an inflation fluid,
    wherein the inflatable balloon is disposed entirely within the inflation tube when in the unexpanded configuration and is disconnected from the inflation tube when in the expanded configuration,
    wherein the inflatable balloon has a triangular shape when in the expanded configuration.

2. The expansion device of claim 1, wherein the inflatable balloon is configured to distend the soft tissue between the two adjacent teeth of the patient to fill a missing gingival tissue area when in the expanded configuration.

3. The expansion device of claim 1, wherein the inflatable balloon is degradable.

4. The expansion device of claim 3, wherein the inflatable balloon is biologically resorbable.

5. The expansion device of claim 1, wherein the inflation fluid includes an agent to facilitate regeneration of gingival tissue.

6. The expansion device of claim 5, wherein the agent is selected from the group consisting of rhGDF-5, PDGF, TBFb, FGF-18, BMP-2, BMP-7, CD-RAP, and combinations thereof.

7. The expansion device of claim 5, wherein the agent is delivered in solution.

8. The expansion device of claim 5, wherein the agent is delivered in a carrier material.

9. The expansion device of claim 1, wherein the inflation fluid includes at least one anti-bacterial agent.

10. The expansion device of claim 1, wherein the inflation fluid includes at least one anti-microbial agent.

11. The expansion device of claim 1, wherein the inflation fluid is configured to cure after the inflation fluid is inserted into the inflatable balloon.

12. The expansion device of claim 1, wherein the inflatable balloon is self-sealing such that the inflatable balloon will seal itself to maintain the inflatable balloon in the expanded configuration.

13. The expansion device of claim 1, wherein the inflation tube is flexible.

14. The expansion device of claim 1, wherein the inflation tube comprises a clear material such that the inflatable balloon is visible through the inflation tube when in the unexpanded configuration.

15. The expansion device of claim 1, wherein the inflation material comprises a statin.

16. An expansion device for treatment of black triangle disease, comprising:
    an inflatable balloon moveable from an unexpanded configuration to an expanded configuration configured to pass through soft tissue between two adjacent teeth of a patient when in the unexpanded configuration; and
    an inflation tube configured to retain at least a portion of the inflatable balloon therein having an entry port for an inflation fluid;
    wherein the inflatable balloon is disposed entirely within the inflation tube when in the unexpanded configuration and is disconnected from the inflation tube when in the expanded configuration;
    wherein the inflatable balloon has a triangular shape when in the expanded configuration;
    wherein the inflatable balloon distends the soft tissue between the two adjacent teeth of the patient to fill a missing gingival tissue area when in the expanded configuration;
    wherein the inflatable balloon is degradable and/or biologically resorbable;
    wherein the inflation fluid includes an agent to facilitate regeneration of gingival tissue selected from the group consisting of rhGDF-5, PDGF, TBFb, FGF-18, BMP-2, BMP-7, CD-RAP, and combinations thereof delivered in a solution or a carrier material; and
    wherein the inflation fluid further includes at least one anti-bacterial agent and/or at least one anti-microbial agent.

* * * * *

UNITED STATES PATENT AND TRADEMARK OFFICE
CERTIFICATE OF CORRECTION

| | | |
|---|---|---|
| PATENT NO. | : 8,734,387 B2 | Page 1 of 1 |
| APPLICATION NO. | : 13/349747 | |
| DATED | : May 27, 2014 | |
| INVENTOR(S) | : Drapeau et al. | |

It is certified that error appears in the above-identified patent and that said Letters Patent is hereby corrected as shown below:

On the Title Page, Item (57), under "ABSTRACT", in Column 2, Line 5, delete "The an expansion" and insert -- The expansion --, therefor.

In the Specification

In Column 8, Line 26, delete "polymycin" and insert -- polymyxin --, therefor.

In Column 9, Line 44, delete "pyridinylamino)" and insert -- pyridinylamino] --, therefor.

In Column 9, Line 51, delete "bupivicaine," and insert -- bupivacaine, --, therefor.

In Column 9, Line 55, delete "mepiridine," and insert -- meperidine, --, therefor.

In Column 11, Line 10, delete "sodiumr;" and insert -- sodium; --, therefor.

In Column 11, Line 11, delete "natainycin;" and insert -- natamycin; --, therefor.

In Column 11, Line 15, delete "nifiupirinol;" and insert -- nifurpirinol; --, therefor.

In Column 11, Line 44, delete "sulfisboxazole" and insert -- sulfisoxazole --, therefor.

Signed and Sealed this
Fourteenth Day of October, 2014

Michelle K. Lee
*Deputy Director of the United States Patent and Trademark Office*